United States Patent [19]

Kleinwolterink, Jr. et al.

[11] Patent Number: 5,015,237

[45] Date of Patent: May 14, 1991

[54] PNEUMATIC POWERED ANIMAL INJECTOR

[75] Inventors: Henry Kleinwolterink, Jr.; Dixon G. Granstra, both of Sheldon, Iowa

[73] Assignee: Poke, Inc., Sheldon, Iowa

[21] Appl. No.: 435,252

[22] Filed: Nov. 13, 1989

[51] Int. Cl.$^5$ ............................................. A61M 37/00
[52] U.S. Cl. ............................. 604/143; 604/141; 604/147
[58] Field of Search .................... 604/140–141, 604/143–144, 146–147

[56] References Cited

U.S. PATENT DOCUMENTS 4,717,384  1/1988  Waldeisen ........................ 604/143
4,790,624  12/1988  Morrow et al. .................... 604/143
4,861,340  8/1989  Smith et al. ...................... 604/141
4,941,880  7/1990  Burns .............................. 604/143

FOREIGN PATENT DOCUMENTS 2511596  2/1983  France ............................ 604/143
0685283  9/1979  U.S.S.R. .......................... 604/147

Primary Examiner—Stephen C. Pellegrino
Assistant Examiner—Michael Rafa

[57] ABSTRACT

A device for injecting serum or the like into animals while remaining at a distance from the animal. The device uses air pressure from a tank built into the device to eject the serum from a syringe on the tip of the wand. The wand is long enough to provide relative safety for the user.

3 Claims, 3 Drawing Sheets

PNEUMATIC POWERED ANIMAL INJECTOR

BACKGROUND AND SUMMARY OF THE INVENTION

This invention relates to injection devices useful for injecting large animals while the operator is standing a safe distance from the animal. It is particularly useful with livestock such as cattle, hogs, horses or the like.

Most livestock is inoculated with serum against common animal diseases. If the inoculation can be accomplished while the animal is still small (especially hogs), such vaccination poses no problem. However, the young offspring of large animals such as cattle or horses may be relatively large.

Injection of such animals—and certainly of adult animals—can obviously be dangerous. Therefore, a number of devices have been proposed to keep the animal at a distance from the user of the device. Some of the devices have used a hypodermic needle on the end of a wand. Most such devices used the thrust by the operator as the force by which the serum would be forced through the needle. However, when the same force is being used to push the needle through the skin of the animal and to eject the liquid from the syringe, there is always considerable degree of spillage.

The present invention uses the thrust by the operator to force the needle through the animal hide, but then uses an exterior force—preferable compressed air or other gas—to operate the syringe. An easily operated valve means is conveniently located so that a simple press of the thumb causes the plunger of the syringe to force the serum through the hypodermic needle.

DESCRIPTION

Figure 1:
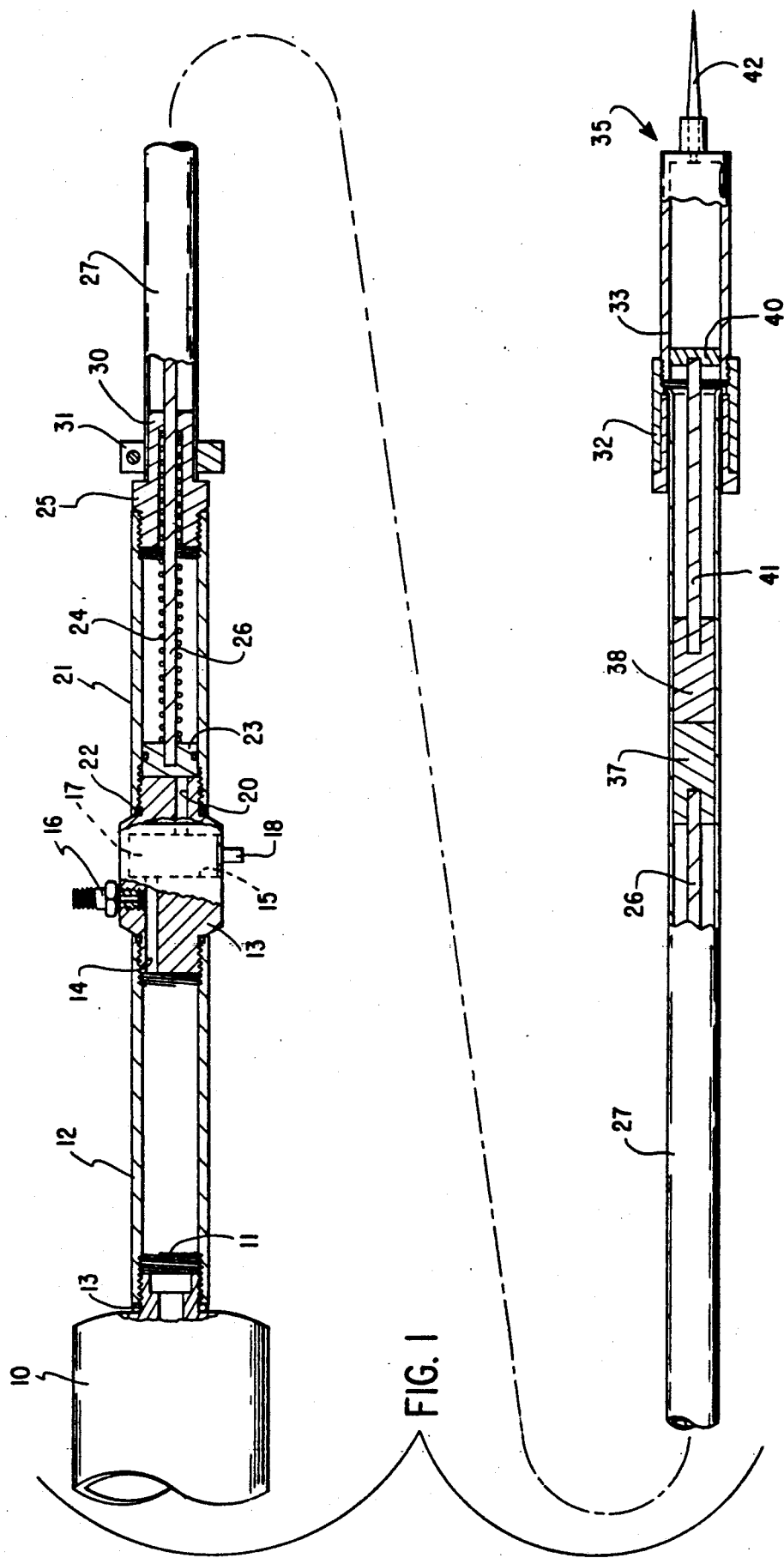
FIG. 1 is a view of the injector of our invention partly in section to show underlying parts.

Briefly our invention comprises a device for injecting large animals from a safe distance, in which the syringe is carried at the end of a wand and is operated by a push rod within the wand. The push rod is actuated by compressed gas carried in a tank formed as part of the tool.

More specifically, the tool includes a compressed air tank 10 of conventional design. Although it will be described as compressed air, it will be obvious that other compressed gases could be used if desired. The tank 10 is customarily provided with a threaded nipple 11 onto which a tube 12 is treaded. An O-ring 13 may be used to seal the joint between the tank 10 and the tube 12. This tube may also serve as a grip by which the operator may hold the device and direct and inject the point of the needle into the animal.

The tube 12 at the end opposite to the tank is threaded to receive a valve housing member 13. This member is drilled to provide a passageway 14 from the tube to a hollowed area 15. A pressurizing check valve 16 similar to the valve on a pneumatic tire may be provided to allow the tank 12 to be re-pressurized from an air compressor (not shown) by use of familiar and readily available fittings.

A valve 17 having an operating member 18 is held within the opening 15. This valve is a two-position valve having a normal position in which it exhausts from one port to the atmosphere and a second operating position in which the passage from the tube 12 to a second passageway 20 in the housing member 13 is opened. The preferred valve of the type known as Clippard—MJV-3C or MJV0-3C. The valve is arranged so that the passageway 20 is normally open, thus closing passageway 14 and holding pressure within the tank 10.

The passageway 20 leads into a cylinder 21 which is threaded onto the housing member 13, and is sealed thereto by an O-ring 22. A piston 23 is slidably disposed in the cylinder 21, and is biased to the position shown in FIG. 1 by a compression spring 24. This spring is seated in a closure member 25 threaded into the cylinder 21 to close and seal the end of the cylinder within which the piston 23 acts. A piston rod 26 acts both to support the spring 24 and to transmit motion to the piston 23. To perform the latter function, the rod 26 extends slidably through the closure 25 and into an extension tube 27.

The extension tube 27 may be clamped onto an extended end 30 of the closure member 25 by means of a clamp 31 surrounding the tube. Because there is no compressed air or the like outward of this part of the device, it is not necessary to provide any seal.

At its outer end, the extension tube or wand 27 carries a ferrule 32 which is threadedly engaged with the cylinder 33 of a veterinary syringe 35. This engagement is such that the syringe may be readily removed to be refilled.

In order to provide operation of the syringe 35, the rod 26 extends from the closure member 25 into the wand 27 and terminates in a bumper slide 37. This slide is slidable within the wand 27 and serves to hold the rod 26 substantially central of that wand. The bumper 37 is in abutting relation with a similar bumper slide 38 also slidably disposed in the wand 27.

The bumper 38 is part of the operating mechanism of the syringe. It is attached to the operating piston 40 of that syringe by a rod 41 so that when the bumper 38 is moved within the wand 27, the piston 40 is similarly moved within the cylinder 33 of the syringe.

Figure 2:
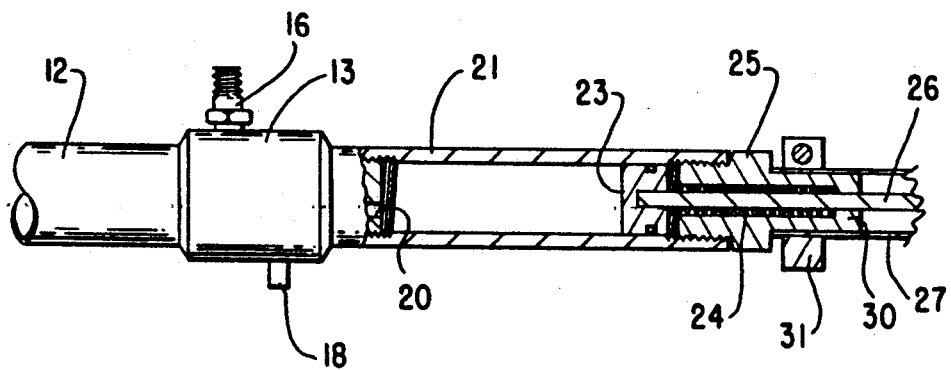
FIG. 2 is a view of the power cylinder portion of the injector showing parts in a secondary position.
Figure 3:
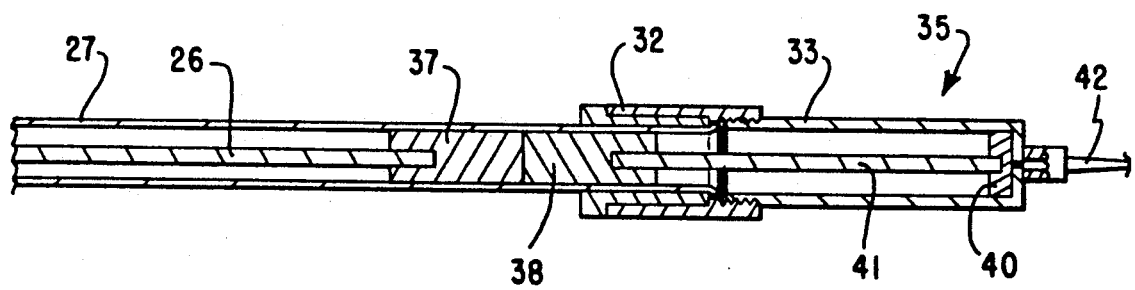
FIG. 3 is a sectional view of the needle end of the injector with parts in position corresponding to FIG. 2.

In operation of the device, the tank 10 is first charged with a compressed gas, ordinarily air, injected into the tank through the valve 16. The syringe is filled with the proper serum by removing the syringe 35 from the wand, removing the piston 40 and pouring the proper amount of serum into the syringe 35 and replacing it. As the animal to be inoculated is approached, the user grasps the tube or grip 12, and stabs the animal with the hypodermic needle 42, and nearly simultaneously presses the operating member 18 of the operating valve 17. By that action, compressed air is allowed to flow into the cylinder 21 causing the piston 23 to move rapidly from the position shown in FIG. 1 to that shown in FIG. 2. This motion is transmitted through the rod 26 to the slide 37, in turn pressing bumper 38 and causing it to move the piston 40 within the syringe 35. That motion expels the serum through the needle 42 to accomplish the desired end. Upon release of the thumb of the operator from the member 18, the gas within the cylinder 21 is exhausted to the atmosphere, and the spring 24 returns the piston 23 to its original position. The mechanism of the syringe 35 can be adjusted when the next dosage of serum is poured in.

Because all of this is accomplished very rapidly, it is clear that we have provided a very convenient and relatively simple device to solve the problem of vaccinating large animals safely and quickly.

Figure 5:
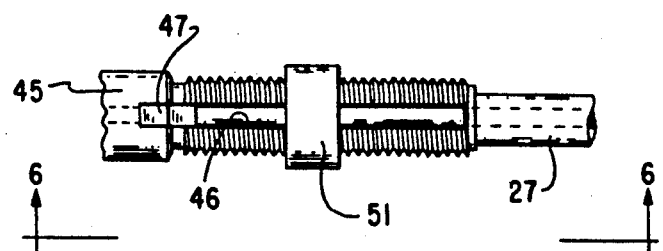
FIG. 5 is a top view of the adjustment mechanism of the alternative of FIG. 4.
Figure 4:
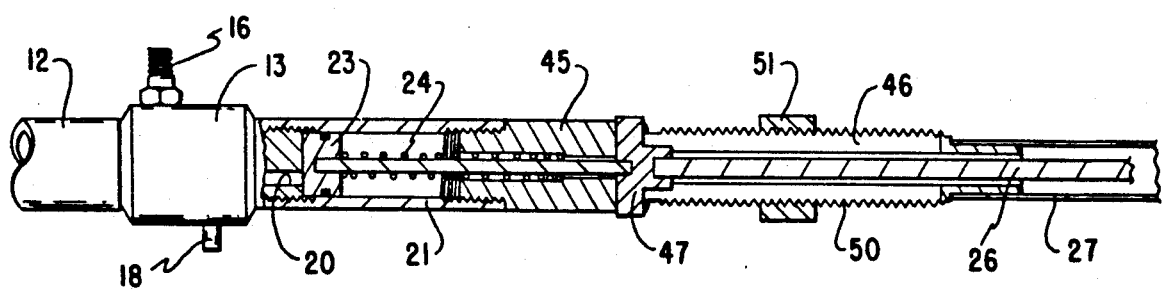
FIG. 4 is a sectional view of an alternative adjustable device which may be used to adjust the dosage.
Figure 6:
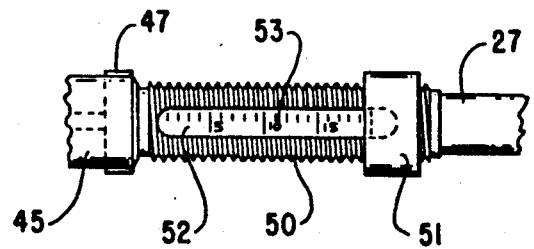
FIG. 6 is view from line 6—6 of FIG. 5 showing a metering scale usable with the alternative of FIG. 4.

An alternative injector for use where variable dosages may be desired is shown in FIGS. 4-6. In this device we use a bushing 15 which is threaded into the cylinder 21. The bushing is formed with a slot 46 in which is journalled a T-shaped striker 47. The rod 26 as used in the previously described embodiment is attached to this striker. A piston rod 48 from the piston 23 in the cylinder 21 extends to and is fastened to the striker 47. Thus, motion of the piston 23 is transmitted through the piston rod 48 to the striker 47 and then to the rod 27.

Threads 50 are formed on the exterior of the bushing 45 at the locale of the slot 46. A threaded collar 51 is engaged with these threads 50 so that the position of the collar can be threadably adjusted. Because the striker 47 extends beyond the outer circumference of the threads 50, movement of the striker can be limited by the position of the collar 51. Thus, movement of the operating piston 40 in the syringe can be adjusted so that variation in the amount of dosage injected into the animal can be controlled. In order to provide a measure for easy control of the adjustment, we provide a flat relief portion 52 on which indicia 53 of the position of the pistons. This scale may readily be calibrated in dosages.

Thus, in addition to a convenient and safe injector, we have provided the flexibility which might be useful for the use of different medicaments for different varieties of animals.

I claim as my invention:

1. A device for vaccinating animals comprising wand means, a supply source of compressed gas attached to one end of said wand means, a pneumatic device having a cylinder and piston assembly attached to said wand means adjacent said supply source; said supply source being connected with said cylinder for transmissions of pneumatic pressure, valve means on said wand means between said supply source and said cylinder, hypodermic injection means attached to the end of said wand means opposite said supply source, said injection means including a piston rod on said piston, striker means on said piston rod, said wand means being formed to provide a slot over a portion of its length, said striker means being slidably journalled in said slot, whereby said pneumatic device operates said injection means, and abutment means adjustably mounted on said wand means adjacent said slot whereby adjustment of said abutment means controls the length of travel of said striker means and therefore of said piston.

2. The device of claim 1 in which said abutment means is threadably engaged with said wand means to provide for its adjustability.

3. The device of claim 2 in which said wand means carries indicia adjacent said abutment means whereby said abutment means can be set to a predetermined position.

* * * * *